(12) United States Patent
Spaargaren et al.

(10) Patent No.: US 8,240,301 B2
(45) Date of Patent: Aug. 14, 2012

(54) DISPENSING DEVICE

(75) Inventors: Jerome Spaargaren, London (GB); Derk Visser, London (GB); Paul Kenneth Rand, Ware (GB); Paul John Turner, Huntingdon (GB)

(73) Assignee: Glaxo Group Limited, Greenford, Middlesex (GB)

( * ) Notice: Subject to any disclaimer, the term of this patent is extended or adjusted under 35 U.S.C. 154(b) by 894 days.

(21) Appl. No.: 12/300,799

(22) PCT Filed: May 24, 2007

(86) PCT No.: PCT/EP2007/055055
§ 371 (c)(1),
(2), (4) Date: Nov. 14, 2008

(87) PCT Pub. No.: WO2007/137991
PCT Pub. Date: Dec. 6, 2007

(65) Prior Publication Data
US 2009/0151721 A1 Jun. 18, 2009

(30) Foreign Application Priority Data
May 31, 2006 (GB) .................................. 0610775.9

(51) Int. Cl.
*A61M 11/00* (2006.01)
(52) U.S. Cl. ............................. 128/200.23; 128/203.12
(58) Field of Classification Search ............. 128/200.11, 128/200.12, 200.14, 200.16, 200.19, 200.21–200.24, 128/202.22, 203.12–203.15, 203.21, 203.23, 128/204.18, 205.23, 207.14
See application file for complete search history.

(56) References Cited

U.S. PATENT DOCUMENTS

| 6,029,659 | A | 2/2000 | O'Connor |
| 7,347,200 | B2 * | 3/2008 | Jones et al. ............. 128/200.23 |
| 7,597,099 | B2 * | 10/2009 | Jones et al. ............. 128/200.23 |

FOREIGN PATENT DOCUMENTS

| GB | 2398065 A | 8/2004 |
| GB | 2411597 A | 9/2005 |
| WO | 03020349 A | 3/2003 |
| WO | 2004039443 A | 5/2004 |

* cited by examiner

*Primary Examiner* — Stephen Crow
(74) *Attorney, Agent, or Firm* — Dwight S. Walker

(57) ABSTRACT

A dispensing device for dispensing a number of doses of medication to a patient, comprising a dispensing mechanism for dispensing the medication by actuation of the dispensing mechanism from a non-dispensing position to a dispensing position, a dose counter for counting the number of doses dispensed by said device, a first battery-less arrangement for providing power to said dose counter in response to the actuation of said dispensing mechanism, and an electronic display for displaying a dose indication, characterised in that the device includes a second battery-less arrangement for providing power to said electronic display when said dispensing mechanism is in said non-dispensing position.

9 Claims, 7 Drawing Sheets

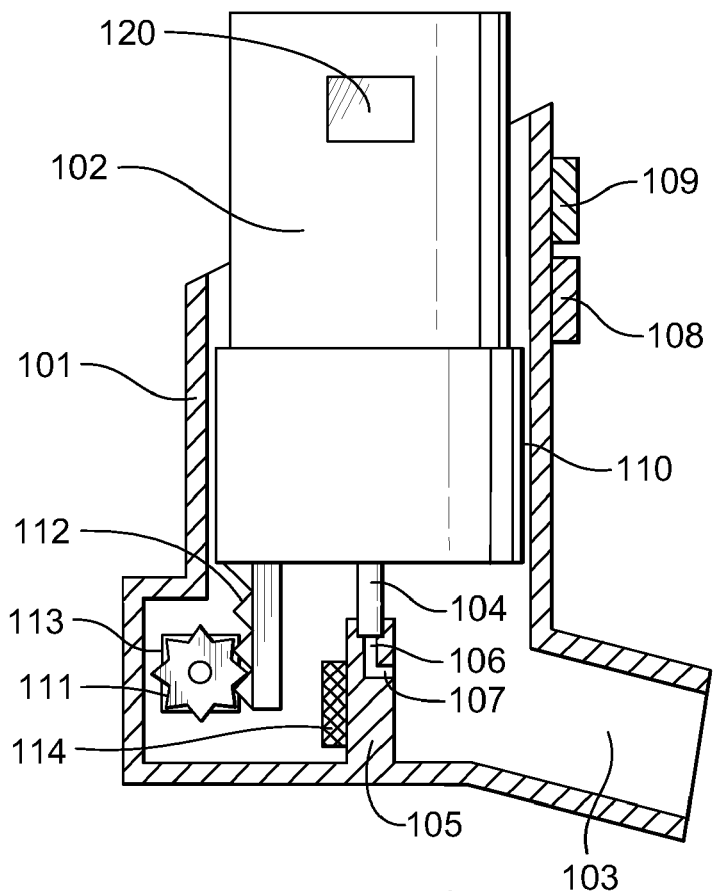
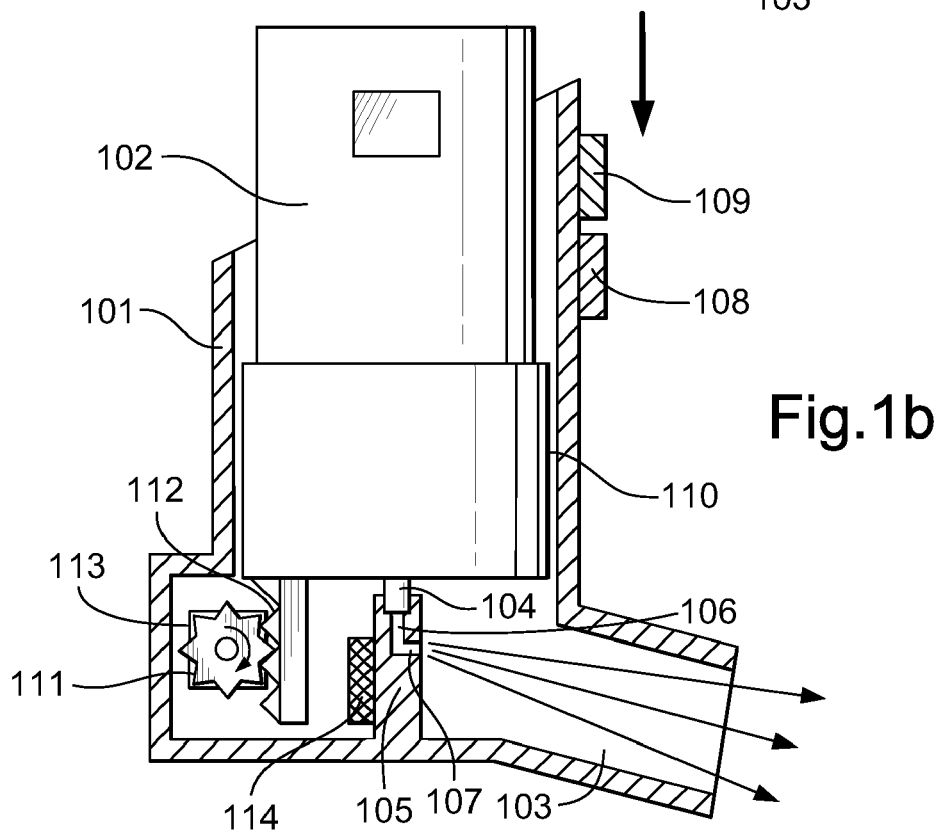

DISPENSING DEVICE

CROSS-REFERENCE TO RELATED APPLICATIONS

This application is filed pursuant to 35 USC 371 as a United States National Phase Application of International Patent Application Serial No. PCT/EP2007/055055 filed on 24 May 2007 which claims priority from GB 0610775.9 filed on 31 May 2006 in the United Kingdom.

FIELD OF THE INVENTION

The present invention relates to a dispensing device for dispensing a number of doses of medication to a patient.

BACKGROUND OF THE INVENTION

Dispensing devices such as metered dose inhalers (MDI) are well known. They typically include a tubular housing in which an aerosol container is located and an outlet tube leading out of the tubular housing. When used for dispensing medicament which is contained in the aerosol container, the housing is held by the patient in a more or less upright position and the outlet tube is placed in the mouth or in the nose of the patient. The aerosol container is depressed inside the housing to dispense a metered dose of medication from the container which is then inhaled by the patient. The actuation of the container is for instance recorded by an electronic counter in the device which stores the number of doses of medicament remaining or dispensed from the container. The dispensing device comprises an electronic display which is modified each time a metered dose is dispensed. The display provides an indication of the number of distributed metered doses or the number of metered doses remaining to be distributed.

An electronic counter and an associated electronic display of a drug delivery device, such as a dispenser, require a power supply to operate. The power supply is generally a battery mounted in the dispenser. There are however several problems associated with the use of a battery source in a dispenser. First, there is a risk that due to possible premature failure of the battery the electronic counter and the associated electronic display cannot work anymore. Second, it is bulky so that there is a need for space in a dispensing device to accommodate a battery. Third, a battery presents a risk of toxicity in the event of electrolyte leakage. In addition, environmental directives require a battery to be recovered when a used dispensing device is disposed of.

International patent application WO-A-2004/039443 concerns a fluid dispensing device which does not include any battery. The device comprises an electronic circuit which drives a dose indicator. The dose indicator includes a static non-volatile liquid crystal display (LCD) not requiring any energy for maintaining the display unchanged in a stationary mode and requiring very low energy to modify the display. An electromechanical generator, such as a piezoelectric actuator or an electromagnetic coil, provides the low energy required to energize the electronic circuit and to modify the display during actuation of the dispenser.

A disadvantage of static non-volatile LCD displays is that they are expensive compared to standard LCD displays. The term "standard LCD display", as used in this document, refers to a display which requires power to be readable. A further disadvantage is that an insufficient amount of power may be generated during actuation of the dispenser to modify the displayed value on the static non-volatile LCD display It would thus be desirable to provide a dispensing device including a relatively cheap LCD display which is operable by a battery-less arrangement.

SUMMARY OF THE INVENTION

In accordance with a first aspect of the present invention, there is provided a dispensing device for dispensing a number of doses of medication to a patient, comprising a dispensing mechanism for dispensing the medication by actuation of the dispensing mechanism from a non-dispensing position to a dispensing position, a dose counter for counting the number of doses dispensed by said device, a first battery-less arrangement for providing power to said dose counter in response to the actuation of said dispensing mechanism, and an electronic display for displaying a dose indication, characterised in that the device includes a second battery-less arrangement for providing power to said electronic display when said dispensing mechanism is in said non-dispensing position.

The invention provides a dispensing device including in combination a first battery-less arrangement for providing power to the dose counter when a dose of medication is being dispensed and a second battery-less arrangement, such as a photoelectric converter, for providing power to the electronic display when a dose of medication is not being dispensed so that a user (e.g. a patient or healthcare provider) can read or view the display in-between dispensing events.

The solution of the invention has the advantage that the electronic display can be a standard LCD display which is less expensive than a static non-volatile display. Another advantage is that a standard LCD display requires less power to modify the displayed value than a static non-volatile display. A further advantage is that the electronic dose counter and the electronic display of the dispensing device do not require any battery to operate.

In one embodiment, the first battery-less arrangement for providing power to the dose indicator include an electromechanical generator.

In another embodiment, the first battery-less arrangement for providing power to the dose counter and the second battery-less arrangement for providing power to the electronic display include one electromechanical generator.

The second battery-less arrangement for providing power to the electronic display may include an actuator for manually actuating the electromechanical generator. Alternatively, the second battery-less arrangement for providing power to the electronic display may include a force-sensitive mechanism.

The dispensing mechanism of the dispensing device may be manually actuated from the non-dispensing position to the dispensing position for dispensing the medication.

It is to be appreciated that where features of the invention are set out herein with regard to the apparatus according to the invention, such features may also be provided with regard to a method according to the invention, and vice versa.

Further features and advantages of the invention will become apparent from the following description of preferred embodiments of the invention, given by way of example only, which is made with reference to the accompanying drawings.

BRIEF DESCRIPTION OF THE DRAWINGS

FIGS. 1a and 1b are schematic partially cut-away views of a dispensing device in accordance with an embodiment of the present invention.

DETAILED DESCRIPTION OF THE INVENTION

Figure 2A:
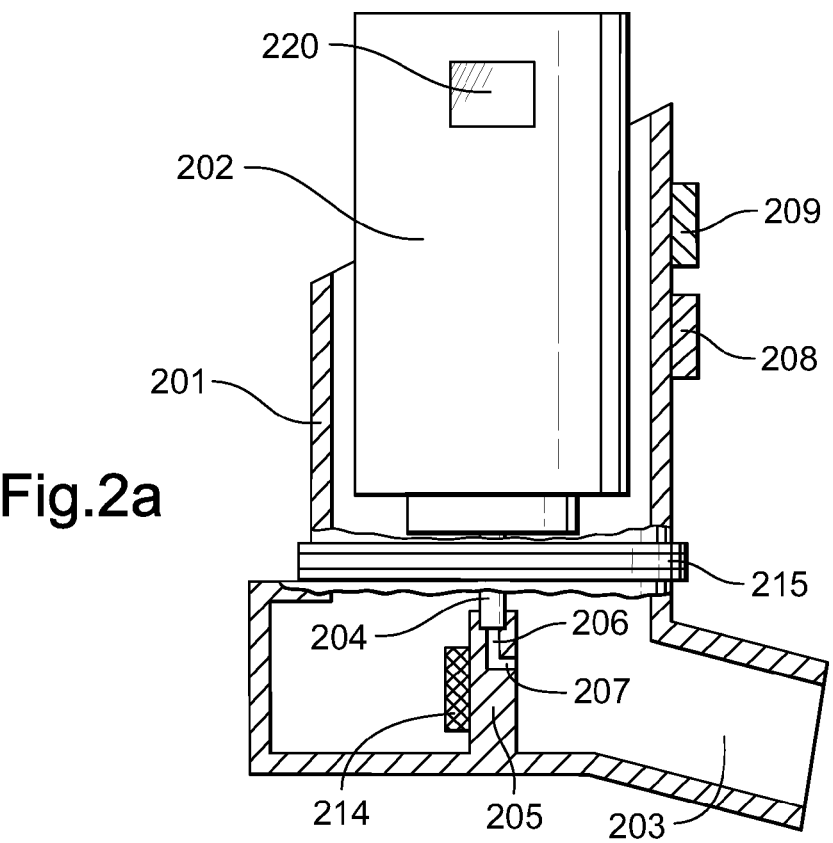
FIGS. 2a and 2b are schematic partially cut-away views of a dispensing device in accordance with a further embodiment of the present invention.

FIG. 1a shows a dispensing device in the form of a metered dose inhaler (MDI) comprises a tubular housing 101 in which an aerosol container 102 can be located. The housing 101 is open at one end (which will hereinafter be considered to be the top of the device for convenience of description) and is closed at the other end. An outlet 103, which is in the form of a mouthpiece intended for insertion into the mouth of the patient, extends laterally from the closed end of the housing 101. The outlet 103 may, if desired, be designed as a nozzle for insertion into the patient's nostril.

The aerosol container 102 has an outlet valve stem 104 at one end. The valve stem 104 can be pressed inside the container to release a measured dose of medication from the aerosol container or, alternatively, the valve stem 104 can be fixed and the main body of the container can be moved relative to the valve stem 104 to release the dose.

The dispensing device comprises a dispensing mechanism for dispensing a medication contained in the aerosol container 102 by manual actuation. As shown in FIG. 1a, the aerosol container 102 is located in the housing 101 so that one end protrudes from its open top. A support 105 is provided in the lower end of the housing 101 and has a passage 106 in which the valve stem 104 of the aerosol container 102 can be located and supported. The passage 106 is connected to a second passage 107 provided in the support 105 and directed towards the interior of the outlet 103.

When the parts are in the positions as shown in FIG. 1a, the dispensing mechanism is in a non-dispensing position. The protruding portion of the aerosol container 102 can be depressed to move the container relative to the valve stem 104 to open the valve. The dispensing mechanism is thus actuated from a non-dispensing position to a dispensing position which is shown in FIG. 1b. A metered dose of medicament is discharged from the valve stem 104 through the passages 106 and 107 and into the outlet 103 from which it can be inhaled by a patient. One metered dose of medication is released from the aerosol container each time it is fully depressed.

An electronic dose counter 120 for counting the number of metered doses dispensed by the container 102 is attached to a location on the aerosol container 102 or is an integral part of the aerosol container 102. The dose counter can increment the count to store the number of doses dispensed, or more preferably, decrement the count to store the number of doses left in the container 102. The dispensing device is preferably arranged such that the dose counter changes the count before the valve 104 opens rather than vice-versa. The reason is that if the counter were set to change after the valve opens, say in response to a detector sensing the dose discharge from the valve, and if the detector failed to detect the dose discharge, the counter would not be decremented even if a dose had been discharged. This could prove confusing to a user as the dose counter would store a number of metered doses left in the container which would be more than the actual number of metered doses left in the container.

The electronic dose counter 120 includes a microprocessor and/or other electronic circuit and a non-volatile memory chip which retains information in the absence of power. Examples of non-volatile memories include flash memory, erasable programmable read-only memory (EPROM), and electrically erasable programmable read-only memory (EEPROM). Electrical contacts (not shown) which are fixed on the aerosol container connect the electronic dose counter to electrical wires (not shown), which in turn connect to an electronic circuit 114 of the dispensing device. The electronic circuit 114 is for instance attached to the support 105 and will be described in further detail in relation to FIG. 3.

A display 108 for displaying a dose indication, preferably a dose count, is attached to a location of the housing 101, or is an integral part of the housing 101. The display is preferably a standard liquid crystal display (LCD), i.e. a display which requires power to be readable.

The invention provides a dispensing device comprising in combination a first battery-less arrangement for providing power to the dose counter in response to the actuation of the dispensing mechanism and a second battery-less arrangement for providing power to the electronic display when the dispensing mechanism is in the non-dispensing position. In the embodiment of the present invention shown in FIGS. 1a and 1b, the first battery-less arrangement is an electromechanical generator which is located inside the housing 101. The electromechanical generator comprises a motor 113 and a drive wheel 111 having a pinion which has an outer circumference defined by a series of teeth, schematically indicated in the Figures. The drive wheel interacts with a rack 112 which is associated with the container 102, in this instance projecting downwardly from a base surface of a sleeve 110, the sleeve being fixedly mounted on the end of the container 102 where the outlet valve stem 104 is mounted. Alternatively, the sleeve 110 is an integral part of the container 102. The toothed rack 112 has a set of teeth which mesh with the teeth of the pinion of the wheel.

FIG. 1b shows the dispensing device of FIG. 1a when actuated by a patient. The downward motion of the container 102 opens the valve 104 for dispensing of a dose of the medication contained in the container 102. As the rack 112 is moved, the rack 110 interacts with the drive wheel 111 to result in electrical energy being generated by the motor 113. The electrical energy is processed by the electronic circuit 114 in order to drive the electronic dose counter 120. The electronic circuit 114 provides sufficient power to the electronic dose counter 120 during a period long enough to allow the electronic circuit of the dose counter to decrement by one the dose count stored in the associated memory. Consequently, the electronic circuit sends a signal to the electronic display 108 in order to show that there is now one less metered dose of the formulation remaining in the aerosol container.

According to the invention, the electronic display 108 is powerable by a second battery-less arrangement. The second battery-less arrangement is preferably a photoelectric converter such as a solar panel 109. The solar panel 109 is attached to a location of, or is an integral part of, the housing 101. The electronic display 108 and solar panel 109 may be fixed side-by-side. The electronic display 108, the solar panel 109 and the motor 113 are each connectable to electrical wires (not shown), which in turn are connectable to the electrical circuit 114 of the dispensing device.

At the completion of the dispensing of the medication dose, the patient releases the canister which consequently returns to the position shown in FIG. 1a, for instance by way of an internal valve return spring (not shown) as known in the art.

Other arrangements of the electromechanical generator are envisaged. For instance, the toothed rack 112 may be an integral part of the housing 101 and project upwardly from the bottom of the housing. In that case, the drive wheel 111 and motor 113 are both attached to the sleeve 110 or otherwise associated with the aerosol container. The sleeve may include an aperture into which the rack can slide and interact with the drive wheel 111.

Also, the first and second battery-less arrangements may include the same elements but at least one element is different. For instance, the first and second battery-less arrangements may include the same electromechanical generator but the second battery-less arrangement also includes a photoelectric converter.

Alternatively, the first battery-less arrangement may include a first electromechanical generator. The second battery-less arrangement may include a second electromechanical generator, different from the first one, but the second battery-less arrangement also includes a photoelectric converter.

Figure 2B:
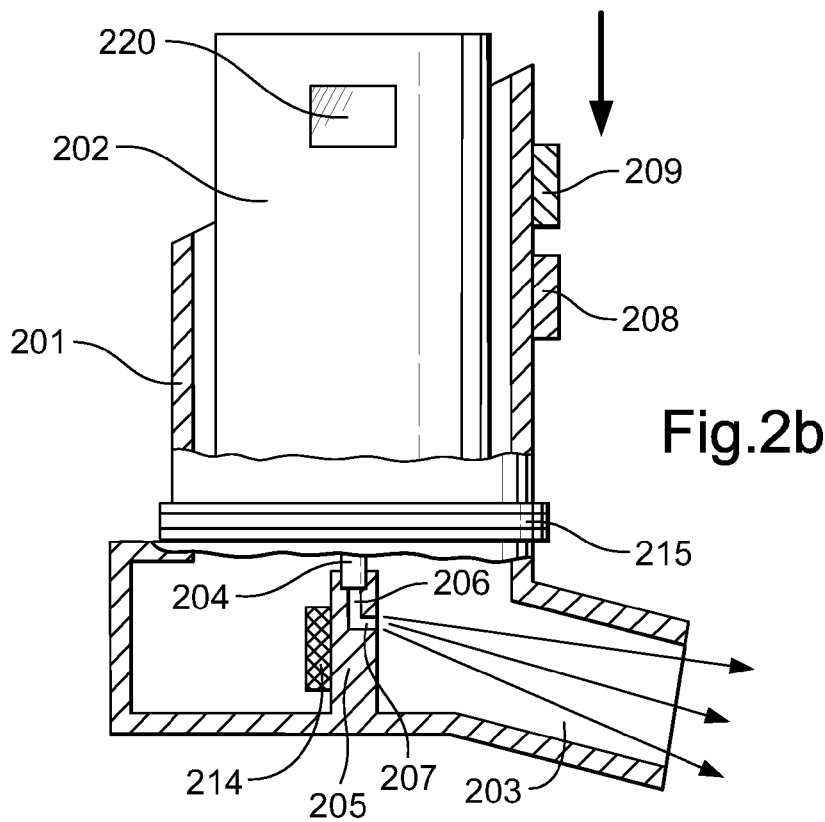

FIGS. 2a and 2b show a device similar to that of FIGS. 1a and 1b but comprising a different type of electromechanical generator according to a further embodiment of the present invention.

The reference numbers of similar components to FIGS. 1a and 1b have been incremented by 100, and the relevant description of those components above should be taken to apply.

In this embodiment, the electromechanical generator, referred as the first battery-less arrangement, is an inductive displacement transducer which comprises an inductive element. The inductive element is suitably an electrically conductive material, preferably a metal, more preferably copper or stainless steel. In another aspect, the electrically conductive material is a conductive polymeric material. The electrically conductive material is connectable as the inductive element in the electronic circuit which will be described below in further detail in relation to FIG. 3.

As shown in FIG. 2a, the inductive displacement transducer comprises an inductive element 215 an electrically conductive material, the material being a wire or tape formed into a coil which is either a flat coil or a helical coil. The coil is firmly attached to the exterior of the housing 201. The turns of the coil may be electrically insulated from each other by the presence of an electrically insulating coating or by embedding in an electrically insulating material or by sufficient spacing of the turns of the coil such that the air between the turns of the coil acts as an electrical insulator. The container may, for example, be comprised of a magnetic or electronically conductive material such as aluminium, or alternatively the container may have attached thereto a magnetic or electronically conductive component. The component may, for example, be a ring of material such as a ferrite ring or the component may be a coating or cover of suitable material.

FIG. 2b shows the dispensing device of FIG. 2a when actuated by a patient with the dispensing mechanism in the dispensing position. On actuation of the device, the protruding portion of the aerosol container 202 is moved relative to the housing and the inductive coil 215 attached thereto. As mentioned above, the container is comprised of or has attached thereto a material so that movement of the container 202 relative to the coil 215 is capable of providing power.

As described in relation to FIGS. 1a and 1b, the electromechanical generator provides sufficient power to the electronic dose counter during a long enough time to allow the microprocessor to decrement by one the dose count stored in the memory. Consequently, the microprocessor sends a signal to the electronic display 208 showing that there is now one less metered dose of the formulation remaining in the canister. The electronic display is powerable by a second battery-less arrangement, different from the first battery-less arrangement, the second battery-less arrangement being a solar panel 209.

At the completion of the dispensing of the medication dose, the patient releases the canister which consequently returns to the position shown in FIG. 2a.

A variety of means of attachment of the inductive element 215 to the housing are envisaged including mechanical grips, adhesive attachments, use of welded shrink sleeves, heat forming, crimping, ultra-sonic welding and by the presence of an o-ring elastomer on the housing which is fixedly piercable by barbs on the attachment member of the inductive displacement transducer. Permanent means are preferred.

In another embodiment, the inductive element 215 is provided with mounting means for mounting the inductive element to the housing. The mounting means may comprise a carrier sleeve mountable on the exterior of the housing and separable therefrom.

In a further embodiment, the inductive coil may be attached to the support 205 at the lower end of the housing 201.

Figure 3:
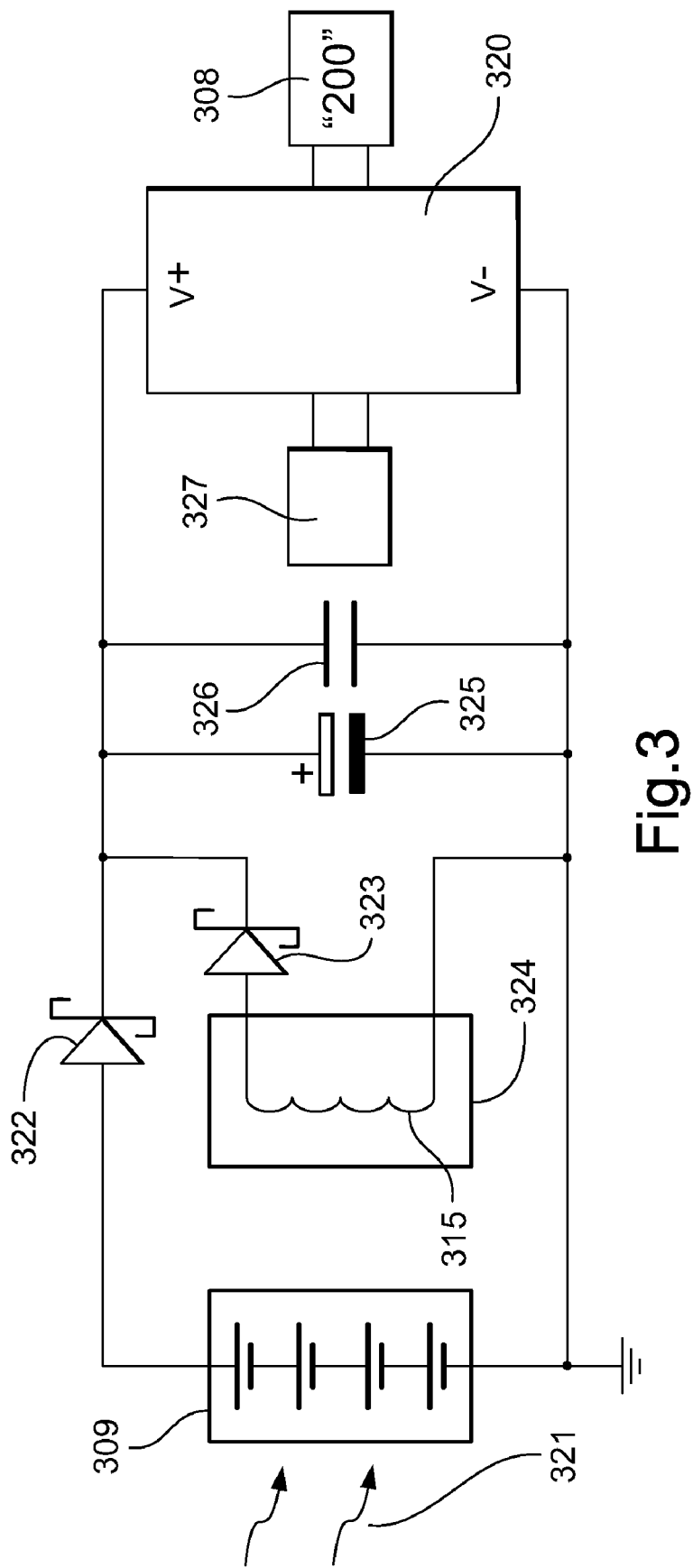
FIG. 3 is a schematic diagram showing an electronic circuit and components of a dispensing device according to an embodiment of the present invention.

FIG. 3 is a schematic diagram showing an electronic circuit and other elements of a dispensing device according to an embodiment of the present invention. The electronic circuit was referred in the previous embodiments as reference numeral 114, 214. In this particular embodiment, the dispensing device comprises a first battery-less arrangement for powering the dose counter, the first battery-less arrangement being an inductive displacement transducer 324 including one or more inductive elements 315 such as described in relation to FIGS. 2a and 2b. The dispensing device includes a second battery-less arrangement, such as a solar panel 309. Using the electronic circuit, the solar panel powers an electronic display 308 upon incident light 321 being captured by the solar panel 309. Also, when the dispensing mechanism is actuated to dispense medication, the inductive displacement transducer 324 provides power to storage means of the electronic circuit such as a reservoir capacitor 325. A dose counter 320 comprising an electronic circuit and a memory is able to use this stored power as if it were a steady supply available from a battery. The electronic circuit included in the dose counter 320 decrements by one the dose count stored in the memory. The electronic display 308 is also updated by the electronic circuit to provide an indication of the number of dispensed metered doses or the number of metered doses remaining to be dispensed from the canister. In the electronic circuit, a pair of Schottky diodes 322, 323 ensures that the electronics are powered by whichever battery-less arrangement has the higher voltage whilst preventing reverse biasing of the solar panel 309 or current drain through the inductive displacement transducer 324. Also, a decoupling capacitor 326 is used in the electronic circuit to decouple the dose counter 320 from noise which may be present in the power supplied by the reservoir capacitor 325.

In a preferred embodiment, there is enough power generated by the second battery-less arrangement when the device is actuated to power one or more other functions of the dispensing device. The power generated by the first battery-less arrangement is for instance used to power a dose detector 327 which is also included in the electronic circuit. The dose detector detects emission of a dose of medication from the container, using for instance a temperature sensor, an acoustic sensor or a switch. The dose detector may be mounted in the vicinity of the valve stem 204 of the container 202 or in the outlet 203 of the housing 201. The electronic circuit of the dose counter 320 decrements by one the dose count stored in the memory only if the dose detector 327 senses dose emission. The actuation of the device generates power for a sufficient time to allow the dose detector 327 to detect dose emission and, if dose emission is detected, for the dose count in the electronic circuit to be decremented before the power stored in the reservoir capacitor 325 runs out.

Figure 4A:
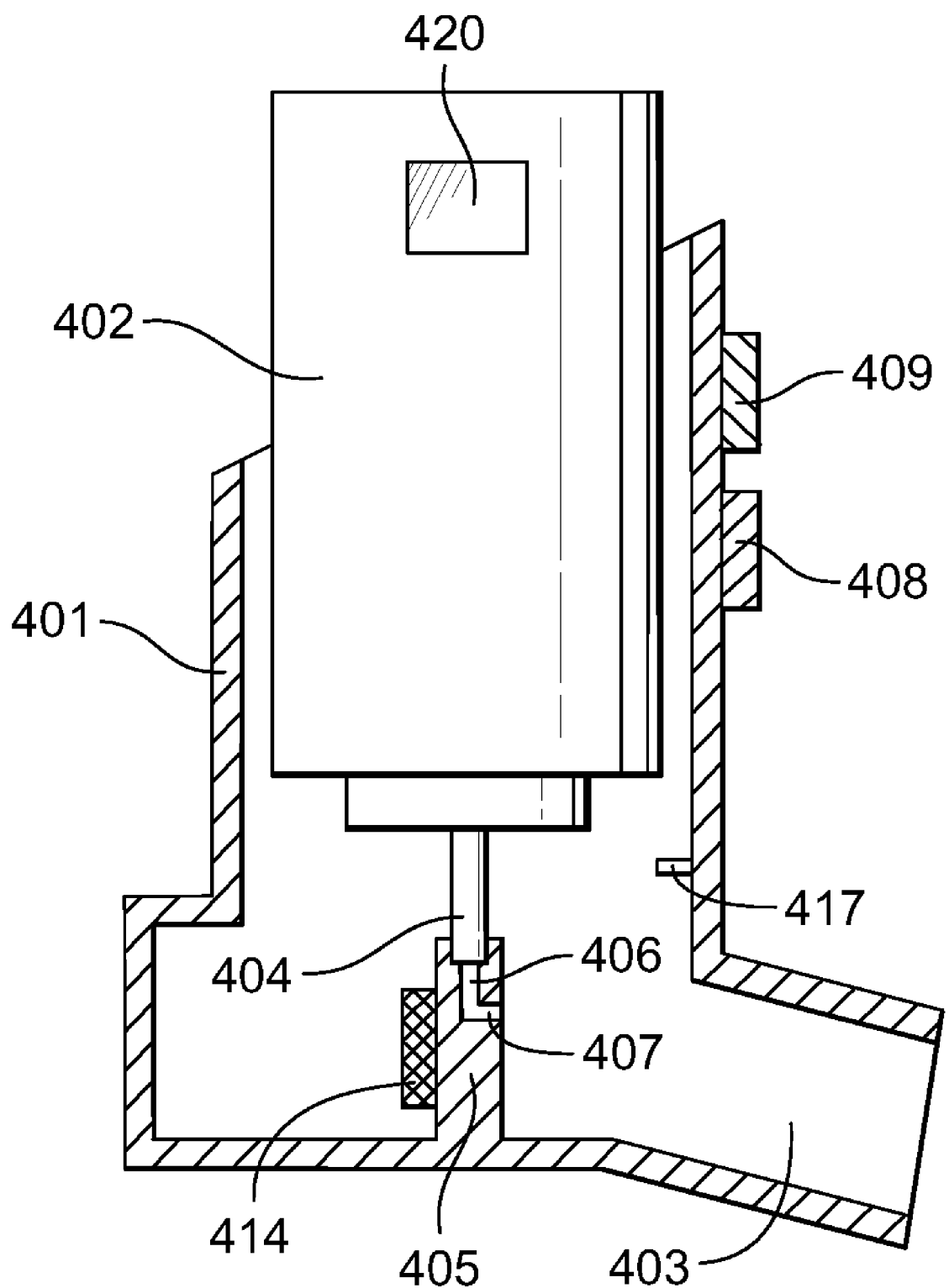
FIGS. 4a to 4c are schematic partially cut-away views of a dispensing device in accordance with another embodiment of the present invention.
Figure 4B:
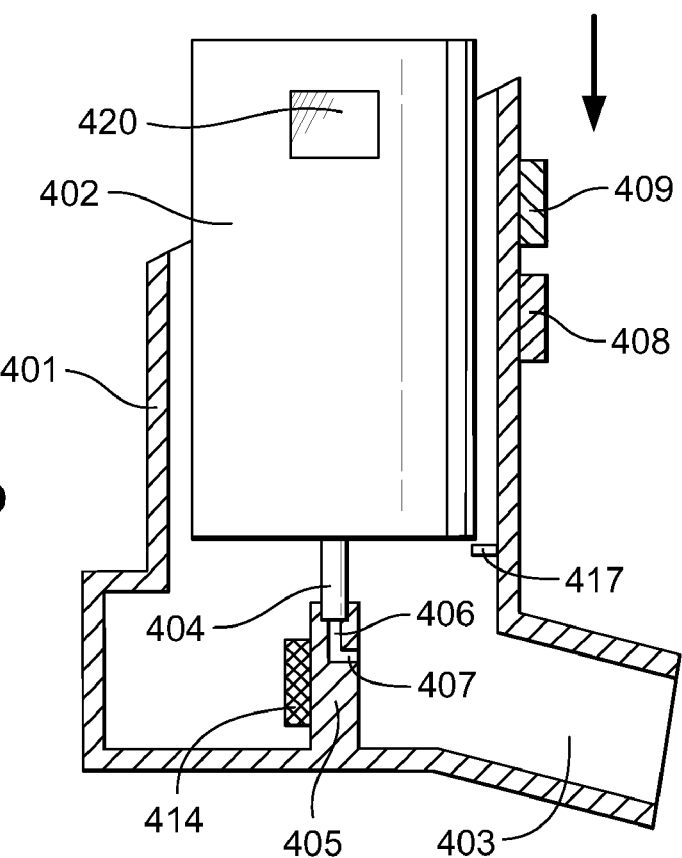
Figure 4C:
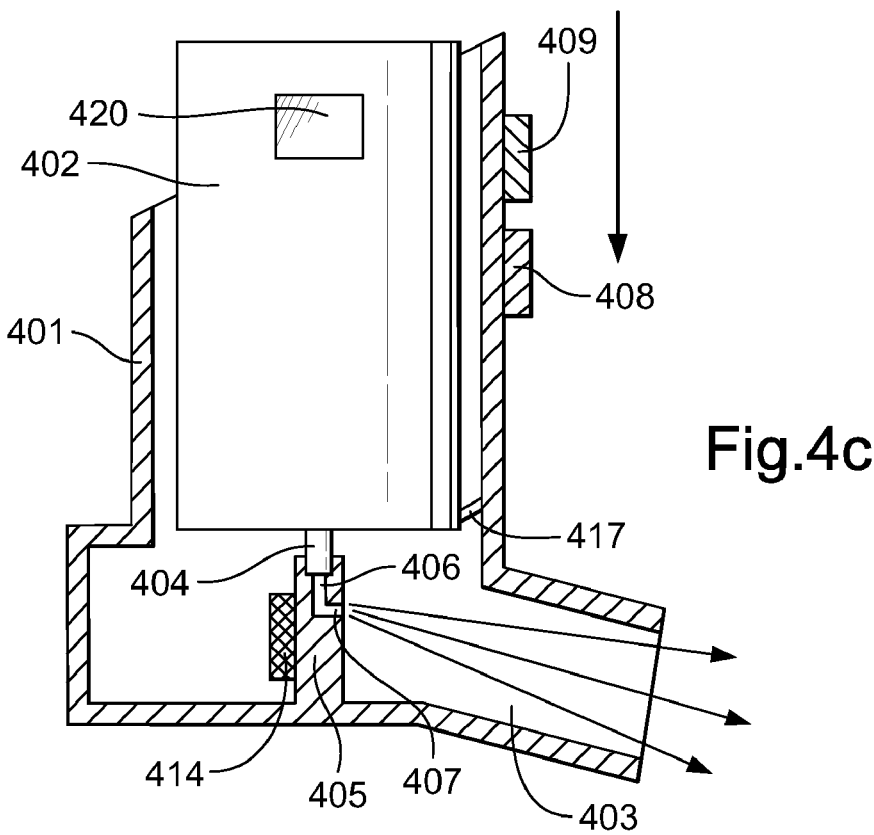

In the specific embodiment shown on FIGS. 4a to 4c, the invention provides a dispensing device in which power can be generated when the dispensing device is in a non-dispensing position. The dispensing device represented in FIG. 4a comprises first battery-less arrangement for providing power to the dose counter and second battery-less arrangement for providing power to the display, both battery-less arrangements including the same electromechanical generator (not shown), e.g. a rack and pinion assembly or an inductive displacement transducer as described in relation to FIGS. 1 and 2. The dispensing device includes a range of non-dispensing positions such as shown in FIGS. 4a and 4b. The second battery-less arrangement also includes a force-sensitive mechanism distinguishing the range of non-dispensing positions and the dispensing position, the actuation of the dispensing mechanism providing power to the electronic display 408 when the dispensing mechanism is within said range. FIG. 4b shows the dispensing device of FIG. 4a when the aerosol container 402 is partially depressed. When the aerosol container 402 is partially depressed, the electromechanical generator is capable of generating power to power the display 408 without the dispenser dispensing any dose of medication. The force sensitive mechanism includes a flexible stopping element 417 which is provided on the inner wall of the housing and which retains the canister to an intermediate/partially depressed position. In a preferred embodiment, the electronic display 408 comprises backlighting, such as in mobile telephones, which is powered when the aerosol container is partially depressed as in FIG. 4b. This feature is useful when the patient is in a dark environment and needs to read the display without any medication being dispensed.

FIG. 4c shows the dispensing device of FIGS. 4a and 4b when the canister is fully depressed. When the patient has applied a predetermined force to overcome the action of the stopping element 417 which is consequently flexed, a dose of medication is dispensed. The first battery-less arrangement provides power to the dose counter. Electrical means are provided for causing the flexure of the stopping element 417 to send a dose count signal to the electronic circuit which is included in the dose counter 420, the electronic circuit decrementing by one the dose count stored in the memory. The stopping element 417 in this embodiment may for instance be a piezoelectric strip. The display 408 is also updated by the electronic circuit to provide an indication of the number of distributed metered doses or the number of metered doses remaining to be distributed from the canister. At the completion of the dispensing of the medication dose, the patient releases the canister which consequently returns to the position shown in FIG. 4a.

The second battery-less arrangement for providing power to the display may also comprise a photoelectric converter such as a solar panel 409.

Alternatively, a cap or a pivoted cover fitted on the outlet tube 403 may limit the displacement of the canister inside the housing. When the cap or cover is on the outlet tube, movement of the canister is limited to an intermediate position which corresponds to a non-dispensing position. When the cap is removed or on opening of the cover, the patient may depress the aerosol container further downwardly inside the housing to dispense a dose of medication from the container. This corresponds to a dispensing position. In the further embodiment shown in FIG. 5a, the dispensing device comprises first battery-less arrangement such as an electromechanical generator, e.g. a rack 512 and drive wheel 511 assembly, which can be actuated by the dispensing mechanism. The drive wheel 511 interacts with the rack 512 projecting downwardly from a base surface of a sleeve 510. The invention provides a dispensing device in which the second battery-less arrangement for providing power to the electronic display includes the same or a second electromechanical generator and an actuator. The actuator may be a button 515 on the device for manually actuating the electromechanical generator, the actuator being different from the dispensing mechanism. The button allows power to be generated when the dispensing device is in a non-dispensing position. The button 515 is provided in the lower end of the housing 501. The button 515 is linked to the drive wheel 511 and motor 513 assembly so that when the button is depressed inside the housing 501, the wheel and motor assembly is pushed upwards inside the housing. The second battery-less arrangement for providing power to the display may also comprise a photoelectric converter such as a solar panel 509.

Figure 5A:
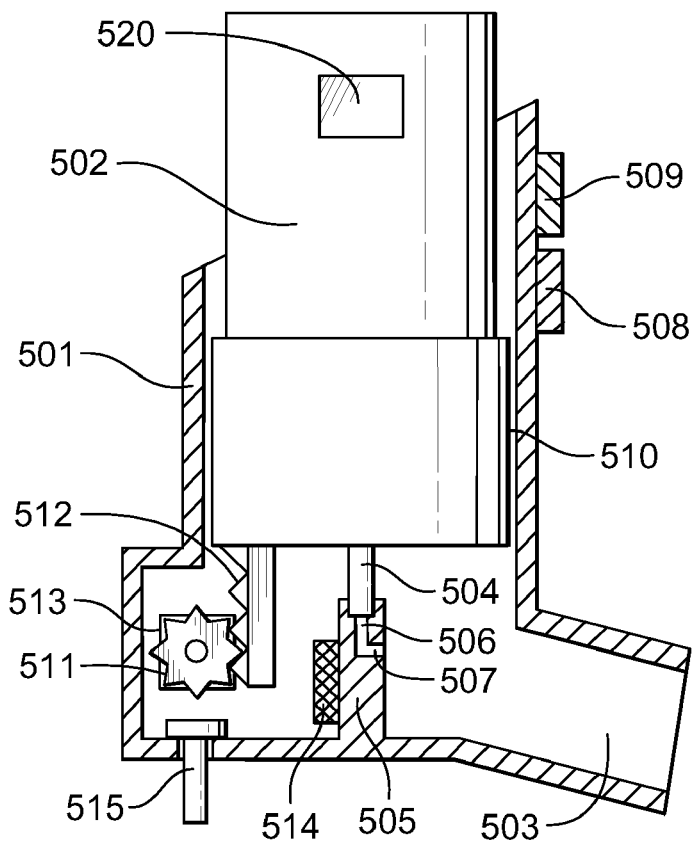
FIGS. 5a and 5b are schematic partially cut-away views of a dispensing device in accordance with a further embodiment of the present invention.
Figure 5B:
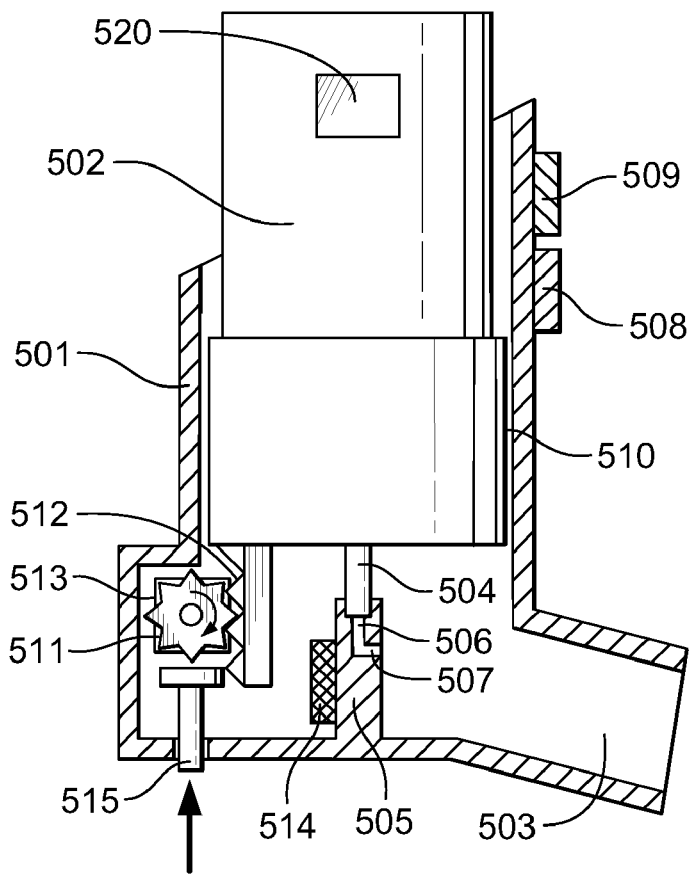

FIG. 5b shows the dispensing device of FIG. 5a when the button 515 is depressed inside the housing. The rack 512 interacts with the drive wheel 511 to result in a pulse of electricity being generated by the motor 513. The electronic display is consequently powered and readable, but as no medication is being dispensed, the dose indication is not changed. In a preferred embodiment, the electronic display comprises backlighting which is powered when the button 515 is depressed inside the housing.

Figure 6A:
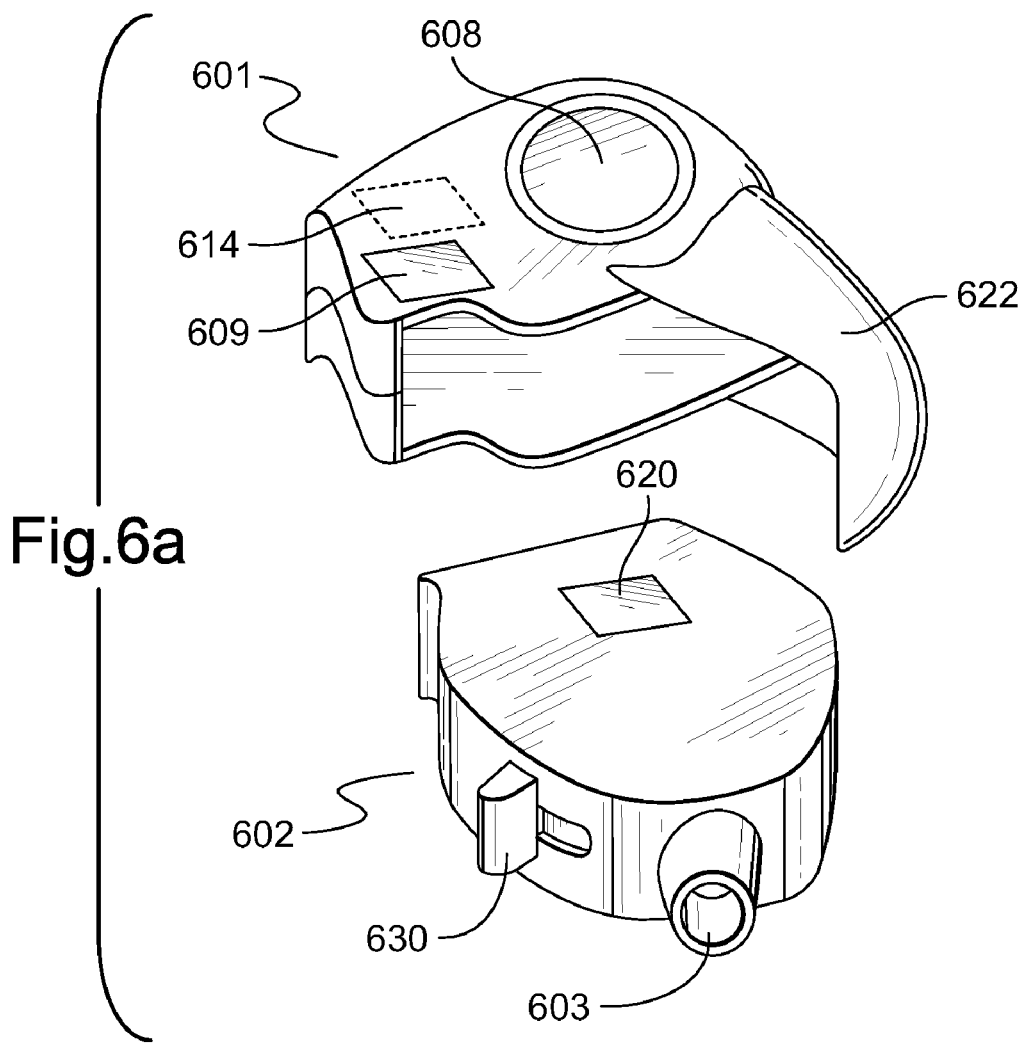
FIG. 6a is a schematic perspective view of a dispensing device in accordance with a further embodiment of the present invention, before assembly.
Figure 6B:
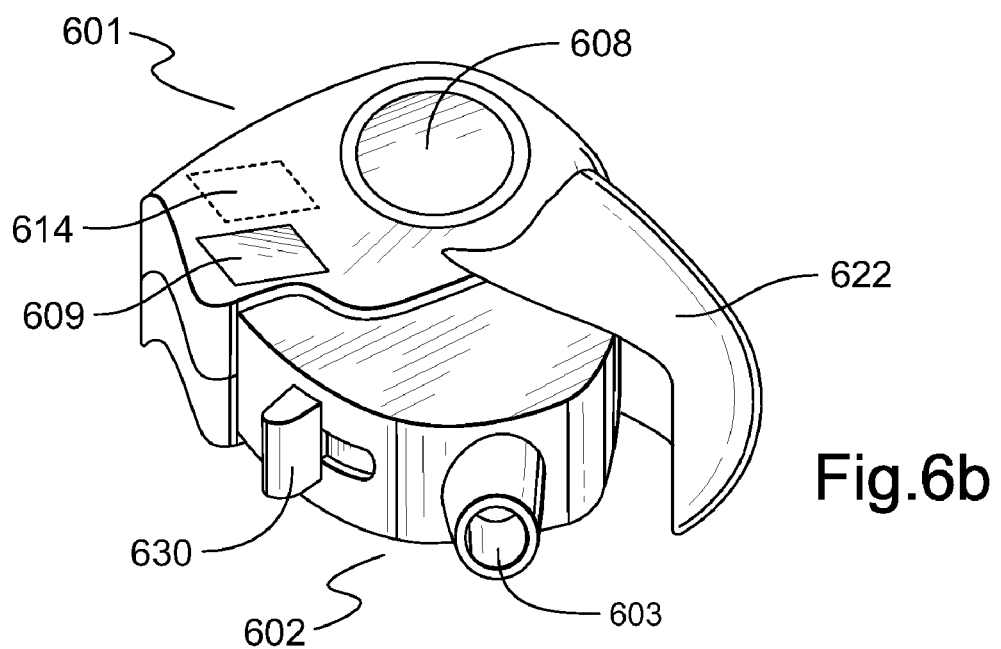
FIG. 6b is a schematic perspective view of the dispensing device of FIG. 6a, after assembly.

FIGS. 6a and 6b show a further embodiment of the invention which is a dispensing device in the form of a dry powder inhaler. A dispensing device of this general type is described in International patent applications WO-A-03/092773 and WO-A-03/092575, the contents of which are included herein by reference. FIG. 6a shows such a device comprising a body or housing 601 within which a removable medicament container 602 may be located. The container 602 comprises an indexing button 630 on the side which is used to actuate an internal dispensing mechanism (not shown) including an indexing wheel for indexing a coiled flexible blister strip (not shown). The flexible strip defines a plurality of pockets, each of which contains a metered dose of medicament in the form of powder which can be inhaled by a user through a mouthpiece 603. An electronic dose counter 620 is attached to a location on the medicament container 602 or is an integral part of the medicament container 602. The dose counter 620 has a non-volatile memory in which a dose count is stored and the dose counter can decrement the count to maintain a stored count of the number of metered doses of medicament left on the flexible strip inside the container 602. The body 601 includes an electronic display 608 for displaying a dose indication and a photoelectric converter such as solar panel 609. Both dose counter 620 and electronic display 608 are driven by an electrical circuit 614 similar to that described in previous embodiments.

FIG. 6b shows the dispensing device with the container 602 in place in the housing 601. The mouthpiece 603 can be accessed by a user by opening a mouthpiece cover 622 mounted on the housing 601 as shown in FIG. 6b. The solar panel 609 is preferably exposed when the cover 622 is opened or closed. Dispensing of a dose of medication is conducted by pressing the indexing button 630 on the side of the container 602 to actuate the internal dispensing mechanism so as to rotate the indexing wheel by one pocket of medicament. The dispensing mechanism of container 602 contains an arrangement for accessing the doses, usually comprising either piercing means or means to peel a lid sheet away from a base sheet of the blister strip. Opening of the strip pocket is configured to occur in an opening station (not shown) of the container 602, the released dose of medicament being inhaled by a user using the mouthpiece 603 which communicates with the opening station.

In one embodiment, pressing of the indexing button 630 in one direction actuates the dispensing mechanism to dispense a dose of medication. A first battery-less arrangement provides power to the dose counter 620 in response to the actuation of the dispensing mechanism and the dose counter 620 is decremented. The first battery-less arrangement operates in a similar way to the previous embodiment described in relation to FIGS. 1a and 1b.

In another embodiment, a second battery-less arrangement is provided in the form of a mechanism whereby actuation of the indexing button 630 in the opposite direction provides power to the electronic display 608 without any dispensing occurring, irrespective of the cover 622 being opened or closed. Alternatively, the second battery-less arrangement may be associated with the mouthpiece cover 622 such that opening of the mouthpiece cover 622 may power the electronic display 608 without any dispensing occurring. The first and second battery-less arrangements may include the same electromechanical generator, such as a ratchet and two pawls assembly (which is well known and will not be described in detail), the first pawl being actuated by the indexing button 630 and the other pawl by opening of the cover 622.

The container 602 described above includes a mouthpiece 603 as a dispensing outlet. The dispensing outlet may alternatively have any suitable form ranging from a simple orifice to a shaped passage (e.g. cone or tube) to a mouthpiece or nozzle. The cover 622 when closed may protect the indexing button 630 to prevent accidental indexing of the medicament container 602.

A medicament dispenser according to the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl] amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy) acetyl]amino}pentanoyl) amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, sabutamol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micron, preferably less than 6 microns. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The above embodiments are to be understood as illustrative examples of the invention. Further embodiments of the invention are envisaged. For example, the invention may be applied to any dispenser or inhaler which may dispense gaseous, liquid, pasty or powdery products or which may dispense tablet products. The medicament carrier may carry medicament in a variety of forms including dry powder, granule, aerosol suspension, solution including aqueous solution, capsule, nebule, pellet and tablet carrier form. The electronic display may provide a dose indication using a graphical display such as a graphic bar. Alternatively, an audible display may provide a dose indication and could be triggered by an interrogation button mounted on the dispensing device. In the specific embodiment shown in FIG. 4a to 4c, the element 417 could be a switch which, in the position of the container within the housing shown in FIG. 4b, is closed so as to trigger a speaker providing an audible dose indication. The dose counter may also be powerable by a piezoelectric crystal. A slip coupling may be provided between the pinion and motor to avoid any damage to the pinion teeth when the aerosol container is pushed in forcefully. A ratchet-pawl assembly may also be provided between the pinion and motor to make use of the rotational energy of the rotor in the motor. Any suitable dose detectors are envisaged including the use of optical sensors and electrical contact switches. The dose detector may sense any parameter affected by release of the medicament such as pressure, temperature, sound, moisture, carbon dioxide concentration and oxygen concentration.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A dispensing device for dispensing a number of doses of medication to a patient, comprising
    a dispensing mechanism for dispensing the medication by actuation of the dispensing mechanism from a non-dispensing position to a dispensing position,
    a dose counter for counting the number of doses dispensed by said device,
    a first battery-less arrangement for providing power to said dose counter in response to the actuation of said dispensing mechanism, and
    an electronic display for displaying a dose indication,
    characterised in that the device includes a second battery-less arrangement for providing power to said electronic display when said dispensing mechanism is in said non-dispensing position.

2. A dispensing device according to claim 1, wherein said first battery-less arrangement includes an electromechanical generator.

3. A dispensing device according to claim 1, wherein, said second battery-less arrangement includes an electromechanical generator.

4. A dispensing device according to claim 3, wherein said first battery-less arrangement and second battery-less arrangement include the same electromechanical generator.

5. A dispensing device according to claim 3, wherein the second battery-less arrangement includes an actuator for manually actuating the electromechanical generator, said actuator being different from the dispensing mechanism.

6. A dispensing device according to claim 2, wherein said electromechanical generator comprises a rack and pinion assembly.

7. A dispensing device according to claim 1, wherein said electronic display is a liquid crystal display.

8. A dispensing device according to claim 1, wherein said dose counter includes an electronic circuit and a non-volatile memory.

9. A method of dispensing a number of doses of medication to a patient using a dispensing device, said dispensing device comprising a dispensing mechanism for dispensing the medication by actuation of the dispensing mechanism from a non-dispensing position to a dispensing position, a dose counter for counting the number of doses dispensed by said device, an electronic display for indicating a dose count, the method comprising:
    operating a first battery-less arrangement for providing power to said dose counter when said dispensing mechanism is in said dispensing position, and
    operating a second battery-less arrangement for providing power to said electronic display when said dispensing mechanism is in said non-dispensing position.

* * * * *